United States Patent [19]

Taylor et al.

[11] Patent Number: 5,094,946
[45] Date of Patent: Mar. 10, 1992

[54] ENZYMATIC PROCESSING OF MATERIALS CONTAINING CHROMIUM AND PROTEIN

[75] Inventors: Maryann M. Taylor, Philadelphia, Pa.; Edward J. Diefendorf, Audubon, N.J.; George C. Na; William N. Marmer, both of Fort Washington, Pa.

[73] Assignee: The United States of America as represented by the Secretary of Agriculture, Washington, D.C.

[21] Appl. No.: 476,843

[22] Filed: Feb. 8, 1990

[51] Int. Cl.⁵ .................... C12P 21/06; C12S 7/00
[52] U.S. Cl. .................. 435/68.1; 435/265; 8/94.27; 210/632; 210/913
[58] Field of Search .............. 435/265, 68.1; 8/94.27; 423/55, 607; 210/632, 913

[56] References Cited

U.S. PATENT DOCUMENTS

| | | | |
|---|---|---|---|
| 3,941,691 | 3/1976 | Romanenko et al. | 210/2 |
| 3,950,131 | 4/1976 | Young | 8/94.27 |
| 4,468,461 | 8/1984 | Bopp | 435/253 |
| 4,483,829 | 11/1984 | Guardini | 423/55 |

FOREIGN PATENT DOCUMENTS

| | | |
|---|---|---|
| 2705671 | 8/1978 | Fed. Rep. of Germany . |
| 212983 | 8/1984 | German Democratic Rep. . |
| 1243784 | 7/1968 | United Kingdom . |

OTHER PUBLICATIONS

Taylor et al., J. Am. Leather Chem. Assoc. 81:4 (1986).
Iliskovic et al., Koza Obuca 34(6):130 (1985) (abstract).
Parvathi et al., Leather Sci., 31:236 (1984) (abstract).
Sivaparvathi et al., Leather Sci., 33:8 (1986).
Parvathi et al., Leather Sci., 33:303 (1986).
Taylor, Maryann, et al., "Enzymatic Treatment of Solid Waste Generated in the Tanning Industry", Abstracts of IVLTCS, 20th Congress Oct. 15–19, 1989.
Taylor, Maryann M. et al., "Enzymatic Treatment of Chrome Shavings" JALCA vol. 84, p. 157, May 1989.
Abstract of Leder- und Hautemarkt., Gerbereiwissenschaft und Praxis, 30, 100 (1978).

Primary Examiner—Charles L. Patterson
Attorney, Agent, or Firm—David R. Sadowski; M. Howard Silverstein

[57] ABSTRACT

Materials containing both chromium and protein and treated by processes which include the steps of: combining a material to be treated (i.e. containing both chromium and protein) with sufficient water to produce a mixture having from about 75 wt. % water to about 95 wt. % water, and an additive which both provides an alkaline pH and provides calcium or magnesium as an enzyme cofactor. The mixture is thereafter held at a temperature of from about 60° C. to about 75° C. for a period of time of from about 0.5 hour to about 4 hours. Subsequently, at least one enzyme is utilized to hydrolyze the protein, thus producing a product containing solubilized hydrolyzed protein and insoluble chromium. After separation of the soluble fraction from the insoluble fraction, the chrome in the insoluble residue may be recycled into the pickling or tanning process, and the essentially chrome-free protein hydrolyzate is potentially useful as an ingredient in feeds, fertilizers, and cosmetics. The processes of the present invention are used to particular advantage to treat wastes from the leather tanning industry, for example, material such as blue stock, chrome shavings, chrome buffing dust, chrome cakes and chrome sludges.

21 Claims, No Drawings

content continues …

ENZYMATIC PROCESSING OF MATERIALS CONTAINING CHROMIUM AND PROTEIN

FIELD OF THE INVENTION

This invention relates to combining a material containing chromium and protein with at least one enzyme which hydrolyzes the protein.

BACKGROUND AND SUMMARY OF THE INVENTION

More than 95% of the leather manufactured in the U.S. is chrome tanned. Disposal of solid chrome wastes from the tanning process has become an increasingly serious problem to the leather industry. Chrome tanning generates approximately 54,000 metric tons of chrome waste annually in the U.S. Sanitary landfills are reluctant to accept chromium-containing waste because of the potential for contaminating ground water with toxic chromium compounds.

Chrome effluent from the bluing stage of leather tanning can usually be treated and then used again in the pickle or in the tan. However, little has been done with solid chrome shavings other than pressing them to form sheet-like products, or possibly hydrolyzing them and recovering the chromium.

Several studies [Aunstrup et al., Brit. Pat. 1,243,784 (1968). Braeumer et al., Ger. Offen. 2,705,671 (1978); Leder- und Hautemarkt. Gerbereiwissenschaft und Praxis 30:100 (1978). Bronowski et al., Leder 30: 8 (1979). Sauer et al., Leder- und Hautemarkt. Gerbereiwissenschaft und Praxis 36: 70 (1984). Iliskovic et al., Koza Obuca 34(6): 130 (1985) have revealed that waste products from fleshing and beaming operations can be treated with enzymes at low temperatures for short periods of time to give products that have commercial value and/or that are acceptable for disposal into municipal sewage systems. In contrast, previously disclosed procedures for treating solid chrome waste products usually are time-consuming or require boiling of the chrome wastes before enzymatic treatment [Suseela et al., Leder 34: 82 (1983); 37: 45 (1986). Parvathi et al., Leather Sci. 31: 236 (1984); 33: 8, 303 (1986). Monsheimer et al., Ger. Offen. 2,643,012 (1978). Hafner et al., Ger. (East) DD 212,983 (1984); DD 243,715 (1987)]. Furthermore, in these processes, chromium is frequently dissolved and becomes difficult to separate from the hydrolyzed protein.

SUMMARY OF THE INVENTION

We have now surprisingly discovered that with utilization of appropriate: additives, pH, temperature and treatment time; materials containing both chromium and protein (e.g. chrome waste from the leather industry) may be treated with enzymes (e.g. commercially available enzymes), at moderate temperatures for a short period of time, to achieve hydrolysis and solubilization of protein without substantial solubilization of the chromium. Optionally, the solubilized hydrolyzed protein may be separated from the insoluble chromium, the chromium may then be recycled into the pickling or tanning process, and the essentially chrome-free protein hydrolyzate is potentially useful as an ingredient in feeds, fertilizers, cosmetics, or simply may be treated as sanitary sewage.

In accordance with our discovery, it is an object of the instant invention to avoid the heating of chrome wastes to a high temperature as required in the aforementioned prior art, and thereby reduce the amount of time and energy required to heat said wastes. In this regard, the instant invention also provides the advantages of avoiding the problems associated with such high temperature waste, and reduces the degree to which such waste needs to be cooled.

It is another object of the invention to provide a process which is far more economical and commercially feasible than the prior art processes, by virtue of the aforementioned avoidance of high temperatures and attendant advantages.

It is another object of the present invention to provide processes for converting chromium containing materials into useful products.

It is also an object of the invention to provide a novel source of chromium for recycling into the pickling and/or tanning process.

It is another object of the present invention to provide such processes which are far more economical, and avoid chromium disposal problems, by virtue of the aforementioned recycling.

Another object of the invention is to provide a source of hydrolyzed protein that can be isolated and purified for incorporation into a variety of products.

It is a further object of the invention to avoid the possible risk of contaminating the environment with toxic chromium compounds that might result from the disposal of chrome wastes from the leather industry.

Surprisingly, the present invention achieves the aforementioned objects and advantages without the chromium poisoning the enzymes.

Other objects and advantages of this invention will become readily apparent from the ensuing description.

DETAILED DESCRIPTION OF THE INVENTION

Material to be treated in accordance with the present invention may contain insoluble chromium, solubilized chromium or both insoluble and solubilized chromium. Insoluble chrome wastes contemplated for treatment by the processes of the present invention include materials such as blue stock, chrome shavings, chrome buffing dust, chrome sludges and chrome cakes that result from effluent recycling. In the present specification and claims, the phrase "chrome shavings" is intended to have its usual and typical meaning in the leather industry i.e. referring to a combination of pieces of animal hide and chromium (including both protein and chromium) produced during chrome tanning of animal hide.

In accordance with the present invention, material to be treated (i.e. material which includes chromium and protein) is first combined with sufficient water to produce a mixture having from about 75 weight % water to about 95 weight % water (preferably from about 77 wt. % water to about 91 wt. % water, and most preferably from about 80 wt. % water to about 91 wt. % water). The material to be treated is combined with water so that the enzyme can hydrolyze the protein. One of the necessary components in hydrolysis is water.

In accordance with a first embodiment of the instant invention the material to be treated is also combined with an additive which includes one or more of: (1) calcium oxide; (2) calcium hydroxide, and; (3) one or more calcium salt in combination with one or more of sodium hydroxide, potassium hydroxide, sodium carbonate and potassium carbonate. The aforementioned additive(s) are utilized in order to both adjust the pH and to provide calcium ions which are a cofactor for the enzymes. The additive is added in an amount sufficient to bring the pH of the mixture into the range of from about 10 to about 11. This pH range is critical because if the pH is too high, the enzyme will be inactivated; if it is too low the chromium will be solubilized. Subsequently, the mixture of the material to be treated, water and additive are held at a temperature of from about 60° C. to about 75° C. (more preferably from about 63° C. to 65° C.) for a period of time from about 0.5 hour to about 4 hours (more preferably from about 1 hour to about 2 hours) so that the pH of the mixture rises until it is in the range of from 10 to about 11 (more preferably from about 10 to about 10.7). At temperatures significantly below about 60° C. the collagen does not denature and therefore the enzyme will not hydrolyze the protein. At temperatures significantly above about 75° C. the enzyme is inactive. The aforementioned period of time is critical to the present invention because this gives sufficient time for the pH and temperature to stabilize for collagen to be denatured in preparation for enzymic hydrolysis.

In accordance with a second embodiment of the present invention, in addition to being combined with the aforementioned proportion of water, the material to be treated is also combined with an additive which includes one or more of: (1) magnesium oxide; (2) magnesium hydroxide, and; (3) one or more magnesium salt in combination with one or more of sodium hydroxide, potassium hydroxide, sodium carbonate and potassium carbonate. The additive is added in an amount sufficient to bring the pH of the mixture into the range of from about 8.9 to about 11. This pH range is critical to the present invention because it is within this range that the enzymes have optimal activity. More specifically, when the additive consists essentially of one or more of magnesium oxide or magnesium hydroxide, it is preferred to utilize an amount of additive sufficient to bring the pH of the mixture into the range of from about 8.9 to about 9.1. Also, when the additive includes one or more of magnesium oxide or magnesium hydroxide and one or more of calcium oxide or calcium hydroxide, it is preferred to utilize an amount of additive sufficient to bring the pH of the mixture into the range of from about 9.2 to about 10.4. Utilization of magnesium oxide in combination with sodium hydroxide is of particular advantage because magnesium catalyzes the reaction more efficiently than calcium, and substitution of sodium hydroxide for some magnesium makes the process more economical. When the additive includes magnesium oxide in combination with sodium carbonate, it is preferred to utilize an amount of additive sufficient to bring the pH of the mixture into the range of from about 9 to about 10. The aforementioned additive not only serves to adjust the pH of the mixture, but also provides magnesium which is a cofactor for the enzymes. Subsequently, the mixture of the material to be treated, water and additive is held at a temperature of from about 60° C. to about 75° C. (more preferably from about 63° C. to about 65° C.) for a period of time from about 0.5 hour to about 4 hours (preferably from about 1 hour to about 2 hours), so that the pH of the mixture rises until it is in the range of from about 8.9 to about 11 (more preferably from about 8.9 to about 10.5).

Both of the aforementioned embodiments include adding to the mixture (subsequent to the holding step) at least one enzyme specific for hydrolysis of the protein. The present invention may employ any of a variety of heat- and alkali-stable proteolytic enzymes. Examples include enzymes having the essential characteristics of the proteases that are available commercially under the name ALCALASE TM (optimal activity at 55°-65° C. and pH 8.3-9.0, Novo Laboratories, Inc., Danbury, Conn.); and proteases having the essential enzymatic characteristics of those available commercially under the names ENZECO TM ALKALINE PROTEASE-L (optimal activity at 50°-70° C. and pH 7.0-11.0, Enzyme Development Div., Biddle Sawyer Corp., New York, N.Y.,); ESPERASE TM (Novo Laboratories, supra); and SAVINASE TM (Novo Laboratories, supra). Of course, any heat- and alkali-stable protease that is useful in hydrolyzing proteins from chrome wastes may be utilized.

The conditions of enzyme treatment, including the enzyme concentration and the time and temperature of reaction, are selected to achieve substantially complete hydrolysis of proteins from the chrome substrate without solubilizing the chrome. It is preferred to carry out the hydrolysis at a pH of from about 8 to about 11 (most preferably from about 8.3 to about 9.3), for a period of time from about 1 minute to about 4 hours (most preferably from about 2 hours to about 3 hours), and at a temperature of from about 50° C. to about 75° C. (most preferably from about 63° C. to about 65° C.).

After completion of the enzymatic treatment, a soluble fraction comprising the protein hydrolyzate (typically containing less than 4.5 ppm chrome) may be separated from the insoluble chromium containing residue by any suitable means, including for example: gravitational settling, filtration or centrifugation. The protein hydrolyzate may be recovered by any of a variety of conventional techniques, and utilized in feeds, fertilizers or cosmetics, or may simply be treated as sanitary sewage. Similarly, chromium can be recovered from the insoluble residue by any conventional procedure, such as solubilizing the separated insoluble chromium with an acid (e.g. sulfuric acid). The chromium sulfate in solution may be used directly in the pickle stage of hide processing or it may be precipitated, dried and used to make up the tan solution. Clearly, this recycling of the chrome is of tremendous significance as it both provides chrome used in the tanning or pickling, and eliminates the need for any chrome disposal. Because useful products can be recovered from both the soluble fraction and the insoluble residue, these products are of course important assets to the inventive processes.

The following examples are presented only to further illustrate the invention and are not intended to limit the scope of the invention which is defined by the claims.

EXAMPLE 1

Blue stock that had been prepared in a laboratory tannery was dried, cut into 0.25 inch pieces, and ground into a fine powder in a "Wiley" mill. A series of aqueous suspensions of the ground blue stock were treated by the following general procedure: 2.5 grams (g) of the dry blue stock were suspended in 12.5 milliliter (ml) of water, lime (i.e. calcium hydroxide) was added in the proportions indicated in (Table I), and the mixture was heated to 60° C. while being shaken. ALCALASE TM enzyme was added in an amount equal to 6% of the weight of blue stock, and incubation at 60° C. was continued for 180 min. The final pH of the treated mixture was measured. The following procedure was utilized in this example and in the following eight examples, for determination of solubility of material treated. The protein hydrolyzate was separated by filtration and stored at 4° C., and the residue was dried in a gravity convection oven at 50° C. for 19 hr. The dry weight of the residue was corrected for undissolved additive (i.e., lime in this example) and for inert carrier from the enzyme. The % residue was calculated on the basis of the dry weight of blue stock.

TABLE I

| Example | % Lime[a] | % Solubility of Blue Stock[a] | Final pH |
|---------|-----------|-------------------------------|----------|
| 1A | 2.2 | 10.52 | 6.50 |
| 1B | 4.4 | 54.37 | 7.09 |
| 1C | 6.6 | 57.06 | 7.53 |
| 1D | 8.8 | 73.16 | 7.93 |
| 1E | 11.0 | 82.46 | 8.20 |
| 1F | 13.1 | 39.72 | 10.26 |
| 1G | 15.3 | 46.34 | 10.63 |

[a]Based on dry weight of blue stock.

EXAMPLE 2

This example illustrates treatment of commercial chrome shavings in accordance with the present invention. The procedures of Example 1 were repeated except that chrome shavings (55% moisture, obtained from commercial tanneries and stored at 4° C. until use) were substituted for the dry ground blue stock, and the amounts of lime were as listed in Table II. The results in the table show that 6% lime (based on the wet weight of the shavings) was required to maintain enzyme activity. This amount corresponds to 13% of the dry weight of shavings, a considerably higher amount than the 10% (dry basis) required for the blue stock (Example 1) and a reflection of the greater acidity (lower pH) of the shavings. Thus, it is important that the amount of lime be adjusted appropriately for the substrate.

TABLE II

| Example | % Lime[a] | % Solubility of Chrome Shavings[b] |
|---------|-----------|-----------------------------------|
| 2A | 0 | 4.29 |
| 2B | 1 | 8.55 |
| 2C | 2 | 12.92 |
| 2D | 3 | 10.40 |
| 2E | 4 | 43.78 |
| 2F | 5 | 58.43 |
| 2G | 6 | 72.35 |
| 2H | 7 | 77.85 |
| 2I | 8 | 65.68 |
| 2J | 9 | 76.56 |
| 2K | 10 | 79.77 |
| 2L | 12 | 78.58 |

[a]Based on wet weight (55% moisture) of chrome shavings.
[b]Based on dry weight of chrome shavings.

EXAMPLE 3

The present example illustrates the effect of various enzyme concentrations on chrome shavings solubility. The procedures of Example 2 were repeated except that 6% lime was used in all the treatments, and the levels of enzyme were as listed in Table III. The results show, that for the specific material treated and for the specific parameters utilized in this example, maximum chrome shavings solubility was obtained with 6% enzyme.

TABLE III

| Example | % Enzyme[a] | % Solubility of Chrome Shavings[b] |
|---------|-------------|-----------------------------------|
| 3A | 0 | 8.95 |
| 3B | 1 | 65.74 |
| 3C | 2 | 66.90 |

TABLE III-continued

| Example | % Enzyme[a] | % Solubility of Chrome Shavings[b] |
|---------|-------------|-----------------------------------|
| 3D | 3 | 69.63 |
| 3E | 4 | 73.61 |
| 3F | 5 | 67.07 |
| 3G | 6 | 80.96 |
| 3H | 8 | 79.97 |
| 3I | 10 | 78.18 |
| 3J | 12 | 77.35 |

[a]Based on wet weight of shavings.
[b]Based on dry weight of shavings.

EXAMPLE 4

This example illustrates the effect of temperature during holding and hydrolysis on chrome shavings solubility. The procedures of Example 3 were repeated except that 6% by weight enzyme based on wet weight of chrome shavings was used in all the treatments, and the temperatures were as listed in Table IV. The results in the table show that below 60° C. solubility is reduced.

TABLE IV

| Example | Temperature (°C.) | % Solubility of Chrome Shavings[a] |
|---------|-------------------|-----------------------------------|
| 4A | 50 | 46.81 |
| 4B | 55 | 55.53 |
| 4C | 60 | 76.66 |
| 4D | 65 | 81.93 |
| 4E | 70 | 83.40 |
| 4F | 75 | 82.53 |

[a]Based on dry weight of shavings.

EXAMPLE 5

This example illustrates the effect of various reaction times on solubility of chrome shavings. The procedures of Example 2 were repeated except that 6% by weight lime based on wet weight of chrome shavings was used in all the treatments, and the incubation times were as listed in Table V. The results in the table show that after 120 minutes under these conditions the solubilization is substantially complete.

TABLE V

| Example | Time (min) | % Solubility of Chrome Shavings[a] |
|---------|------------|-----------------------------------|
| 5A | 0 | 13.78 |
| 5B | 5 | 41.18 |
| 5C | 10 | 49.95 |
| 5D | 20 | 53.67 |
| 5E | 30 | 58.56 |
| 5F | 60 | 61.78 |
| 5G | 90 | 64.32 |
| 5H | 120 | 64.96 |
| 5I | 150 | 68.24 |
| 5J | 180 | 70.10 |
| 5K | 210 | 70.38 |
| 5L | 240 | 68.49 |

[a]Based on dry weight of shavings.

EXAMPLE 6

This example illustrates the use of "Enzeco Alkaline Protease-L". The procedures of Example 2 were repeated except that the amounts of lime were as listed in Table VI, and 4% by weight Enzeco Alkaline Protease-L based on wet weight of shavings was substituted for 6% ALCALASE ™. The results in Table VI show that for the conditions utilized in this example, 7.5% lime provided optimal pH for this enzyme activity.

TABLE VI

| Example | % Lime[a] | % Solubility of Chrome Shavings[b] |
|---|---|---|
| 6A | 6.0 | 69.72 |
| 6B | 6.5 | 71.30 |
| 6C | 7.0 | 73.73 |
| 6D | 7.5 | 79.77 |
| 6E | 8.0 | 64.70 |
| 6F | 8.5 | 68.64 |
| 6G | 9.0 | 75.97 |

[a]Based on wet weight of shavings.
[b]Based on dry weight of shavings.

EXAMPLE 7

The purpose of this example is to illustrate the effects of varying enzyme concentration on chrome shavings solubility. The procedures of Example 6 were repeated except that 7% by weight lime based on wet weight of chrome shavings was used in all treatments, and the levels of Enzeco Alkaline Protease-L were as listed in Table VII. The results were as indicated in Table VII.

TABLE VII

| Example | % Enzyme[a] | % Solubility of Chrome Shavings[b] |
|---|---|---|
| 7A | 0 | 30.65 |
| 7B | 1 | 64.38 |
| 7C | 2 | 69.58 |
| 7D | 3 | 72.08 |
| 7E | 4 | 73.47 |
| 7F | 5 | 72.50 |
| 7G | 6 | 79.20 |

[a]Based on wet weight of shavings.
[b]Based on dry weight of shavings.

EXAMPLE 8

Lime Without Enzyme. The procedures of Example 2 were repeated except that no enzyme was added to the suspensions of chrome shavings. The solubilities obtained in the absence of enzyme are reported in Table VIII along with the differences between these values and those obtained with lime plus 6% by weight ALCALASE TM based on wet weight of shavings (Table II). The "difference" values show the effectiveness of the enzyme in reducing the amount of lime needed to solubilize the chrome shavings.

TABLE VIII

| Example | % Lime[a] | % Solubility of Chrome Shavings[b] | Difference[c] (%) |
|---|---|---|---|
| 8A | 0 | 6.78 | −2.49 |
| 8B | 1 | 11.40 | −2.85 |
| 8C | 2 | 10.61 | 2.31 |
| 8D | 3 | 9.26 | 1.14 |
| 8E | 4 | 9.74 | 34.04 |
| 8F | 5 | 13.18 | 45.25 |
| 8G | 6 | 31.18 | 41.17 |
| 8H | 7 | 56.02 | 21.83 |
| 8I | 8 | 67.21 | −1.53 |
| 8J | 9 | 70.52 | 6.04 |
| 8K | 10 | 77.40 | 2.37 |
| 8L | 12 | 76.66 | 1.92 |

[a]Based on wet weight of shavings.
[b]Based on dry weight of shavings.
[c]Table II solubility minus Table VIII solubility.

EXAMPLE 9

This example illustrates the effectiveness of chrome separation. In a pilot tannery, experiments were scaled up to 100–1000 g per sample instead of the 2.5-g samples in the preceding examples, and treatments were run in a heated shaker box in which the temperature was maintained between 60°–70° C. The protein hydrolyzates were separated by filtration and analyzed for chromium by atomic absorption spectroscopy [Taylor et al., J. Am. Leather Chem. Assoc. 81: 4 (1986)]. From 0.85–4.5 ppm of chromium was found.

EXAMPLE 10

The purpose of this example is to illustrate the effects of: the utilization of enzymes, and various concentrations of enzymes; on the solubility of chrome shavings. For each of 6 samples, 100 parts by weight of chrome shavings were suspended in 500 parts by weight of water (i.e. yielding a suspension having, 16.6 weight % chrome shavings and 83.3 weight % water). Five weight percent magnesium oxide (based on wet weight of shavings) was added to each sample and the samples were mixed at 85 revolutions per minute (RPM) at 60.5° C. for 30 minutes. Then various amounts of ALCALASE TM (% based on wet weight of chrome shavings) (alkaline proteolytic enzyme) as indicated in Table 9 were added, and a control was run without addition of the enzyme. The samples were then shaken at 60.5° C. for 3 hours. Solubility of chromium shavings for the samples of this example, and for the samples of all of the following examples, were determined by the following procedure. Each solution was filtered through Whatman No. 1 filter paper. The residue was dried in a gravity convection oven at 50° C. for 16 hours. Based on the dry weight of the residue corrected (as in Example 1) for undissolved additive (i.e., in this example, magnesium oxide) and the dry weight of the shavings (calculated from moisture determination) the percent solubility of the chrome shavings was calculated. The results were as indicated in Table IX:

TABLE IX

| Sample Number | Weight % ALCALASE TM | % Solubility of Chrome Shavings |
|---|---|---|
| 1 | 0 | 13.68 |
| 2 | 1 | 80.57 |
| 3 | 2 | 82.20 |
| 4 | 3 | 87.31 |
| 5 | 4 | 85.49 |
| 6 | 5 | 88.03 |

EXAMPLE 11

The purpose of this example is to illustrate the effects of: the utilization of magnesium oxide, and various concentrations of magnesium oxide; on the solubility of chromium shavings. For each of 6 samples, 100 parts by weight of chrome shavings were suspended in 500 parts by weight water. The samples were mixed at 85 revolutions per minute at 60.5° C. for 30 minutes with the various concentrations of magnesium oxide as indicated in Table X, and a control was run without magnesium oxide. Six weight percent ALCALASE TM was added to each sample, and the samples were shaken for 3 hours. The results were as indicated in Table X:

TABLE X

| Sample Number | Weight % Magnesium Oxide | % Solubility of Chrome Shavings |
| --- | --- | --- |
| 1 | 0 | 8.94 |
| 2 | 1 | 12.46 |
| 3 | 2 | 42.28 |
| 4 | 3 | 70.76 |
| 5 | 4 | 81.90 |
| 6 | 5 | 88.78 |

EXAMPLE 12

The purpose of this example is to illustrate the effects of: the utilization of calcium hydroxide and magnesium oxide, each alone and in combination, and; various concentrations of each of these compounds each alone and in combination. For each sample, 100 parts by weight of chrome shavings were suspended in 500 parts by weight of water. The samples were mixed for 30 minutes at 85 revolutions per minute at 60.5° C. in the presence of the various concentrations of magnesium oxide and/or calcium oxide as indicated in Table XI (also a control was run without either magnesium oxide or calcium oxide). Six percent by weight of ALCALASE TM was added to each sample, and the samples were shaken for 3 hours. The results were as indicated in Table XI:

TABLE XI

| Weight % Calcium Hydroxide | % Solubility of Chromium Shavings |||||| 
| --- | --- | --- | --- | --- | --- | --- |
| | Weight % Magnesium Oxide ||||||
| | 0 | 1 | 2 | 3 | 4 | 5 |
| 0 | 8.94 | 17.46 | 42.28 | 70.76 | 81.90 | 88.78 |
| 2 | 13.70 | 37.44 | 66.13 | 77.00 | 86.35 | 82.66 |
| 3 | 29.95 | 49.44 | 69.85 | 81.70 | 83.63 | 85.74 |
| 4 | 46.55 | 63.64 | 74.16 | 82.87 | 88.54 | 85.72 |
| 5 | 64.31 | 67.45 | 78.23 | 86.02 | 83.69 | 83.95 |
| 6 | 73.61 | 69.60 | 79.97 | 86.36 | 85.44 | 84.83 |

EXAMPLE XIII

The purpose of this example is to illustrate the effects of: the utilization of enzymes, the utilization of magnesium oxide, and various concentrations of both magnesium oxide and calcium hydroxide; on the solubility of chrome shavings. For each of the samples: 100 parts by weight of chrome shavings, 500 parts by weight of water, and the various concentrations of magnesium oxide and magnesium oxide with calcium hydroxide as indicated in Table XII; were mixed at 85 revolutions per minute at 60.5° C. for 30 minutes. Varying concentrations of ALCALASE TM as indicated in Table XII were added, and the samples were shaken for 3 hours. The results were as indicated in Table XII:

TABLE XII

| Weight % Enzyme | Percent Solubility of Chrome Shavings ||||
| --- | --- | --- | --- | --- |
| | 5 Weight % MgO | 4 wt. % MgO and 2 wt. % Ca(OH)$_2$ | 4 wt. % MgO and 4 wt. % Ca(OH)$_2$ | 3 wt. % MgO and 5 wt. % Ca(OH)$_2$ |
| 0 | 13.68 | 12.12 | 9.18 | 17.66 |
| 1 | 80.57 | 78.98 | 69.90 | 79.13 |
| 2 | 82.20 | 82.19 | 79.82 | 82.98 |
| 3 | 87.31 | 83.91 | 81.04 | 85.55 |
| 4 | 85.49 | 74.96 | 81.88 | 84.59 |
| 5 | 88.03 | 87.14 | 87.60 | 84.66 |

EXAMPLE XIV

The purpose of this example is to illustrate the effects of various concentrations of sodium hydroxide in combination with magnesium oxide, on solubility of chrome shavings. For each sample: 100 parts by weight of chrome shavings, 1000 parts by weight of water, and 1 (one) weight % magnesium oxide based on wet weight of chrome shavings; were stirred on a hot plate at 60.5° C. for 30 minutes. Sodium hydroxide was added to each sample to achieve the concentrations as indicated in Table XIII, and the samples were stirred for 30 minutes. Holding pH was then measured. Six percent by weight ALCALASE TM was added to each sample, and the samples were stirred for 3 hours. Final pH was then measured. The results were as indicated in Table XIII:

TABLE XIII

| Sample Number | Weight % Sodium Hydroxide | % Solubility of Chrome Shavings | Holding pH | Final pH |
| --- | --- | --- | --- | --- |
| 1 | 2.43 | 63.27 | 9.54 | 7.77 |
| 2 | 3.12 | 44.62 | 9.04 | 7.79 |
| 3 | 3.98 | 87.49 | 10.55 | 8.34 |
| 4 | 4.94 | 12.20 | 10.83 | 10.65 |

EXAMPLE XV

The purpose of this example is to illustrate the effects of various concentrations of magnesium oxide on pH and solubility of chrome shavings. For each sample, 100 parts by weight of chrome shavings were suspended in 500 parts by weight of water. An amount of magnesium oxide was added to each sample to provide the concentrations as indicated in Table XIV (a control was also run without magnesium oxide). The samples were then mixed for 30 minutes at 85 RPM and 60.5° C. and holding pH was measured. Six weight % ALCALASE TM based on wet weight of chrome shavings was added to the samples, which were then shaken for 3 hours and final pH was measured. The results were as indicated in Table XIV:

TABLE XIV

| Sample Number | Weight % Magnesium Oxide | Holding pH | Final pH | % Solubility of Chrome Shavings |
| --- | --- | --- | --- | --- |
| 1 | 0 | 3.73 | 3.82 | 8.94 |
| 2 | 1 | 7.10 | 6.52 | 17.46 |
| 3 | 2 | 8.27 | 7.17 | 42.28 |
| 4 | 3 | 9.03 | 7.64 | 70.76 |
| 5 | 4 | 9.04 | 8.05 | 81.90 |
| 6 | 5 | 9.05 | 8.54 | 88.78 |

EXAMPLE XVI

The purpose of this example is to illustrate the effects of, various concentrations of magnesium oxide in the presence of calcium hydroxide, on pH and solubility of chrome shavings. For each sample, 100 parts by weight of chrome shavings were suspended in 500 parts by weight of water. Four weight percent calcium hydroxide, and an amount of magnesium oxide to provide the concentrations as indicated in Table XV were added to each sample (also a control was run without magnesium oxide). The samples were then mixed for 30 minutes at 85 RPM and 60.5° C. Six weight % ALCALASE TM was added to each sample, and the samples were then shaken for 3 hours. The results were as indicated in Table XV:

TABLE XIV

| Sample Number | Weight % Magnesium Oxide | Holding pH | Final pH | % Solubility of Chrome Shavings |
|---|---|---|---|---|
| 1 | 0 | 9.05 | 7.62 | 46.55 |
| 2 | 1 | 9.84 | 7.80 | 63.64 |
| 3 | 2 | 10.00 | 8.06 | 74.16 |
| 4 | 3 | 10.06 | 8.61 | 82.86 |
| 5 | 4 | 10.04 | 8.91 | 88.54 |
| 6 | 5 | 9.97 | 8.99 | 85.72 |

The foregoing detailed descriptions and examples are given merely for purposes of illustration. Modification and variation may be made therein without departing from the spirit and scope of the invention.

We claim:

1. A method comprising,
combining a material to be treated which includes chromium and protein with: (a) sufficient water to produce a mixture having from about 75 weight % water to about 95 weight % water, and; (b) an additive which includes one or more of:
   (1) calcium oxide,
   (2) calcium hydroxide, and
   (3) one or more calcium salt in combination with one or more of sodium hydroxide, potassium hydroxide, sodium carbonate and potassium carbonate; said additive being added in an amount sufficient to bring the pH of the mixture into the range of from about 10 to about 11,
holding said mixture at a temperature of from about 60° C. to about 75° C. for a period of time from about 0.5 hour to about 4 hours so that said mixture has a pH of from about 10 to about 11, and
subsequent to said step of holding, adding to said mixture at least one enzyme specific for hydrolysis of said protein, under conditions sufficient to produce hydrolysis of said protein by said at least one enzyme, so as to produce a product containing solubilized hydrolyzed protein and insoluble chromium, wherein said at least one enzyme is active against said protein at said conditions sufficient to produce hydrolysis of said protein by said at least one enzyme.

2. A method comprising:
combining a material to be treated which includes chromium and protein with: (a) sufficient water to produce a mixture having from about 75 weight % water to about 95 weight % water, and; (b) an additive which includes one or more of:
   (1) magnesium oxide,
   (2) magnesium hydroxide, and
   (3) one or more magnesium salt in combination with one or more of sodium hydroxide, potassium hydroxide, sodium carbonate and potassium carbonate; said additive being added in an amount sufficient to bring the pH of the mixture into the range of from about 8.9 to about 11,
holding said mixture at a temperature of from about 60° C. to about 75° C. for a period of time from about 0.5 hour to about 4 hours so that said mixture has a pH of from about 8.9 to about 11, and
subsequent to said step of holding, adding to said mixture at least one enzyme specific for hydrolysis of said protein, under conditions sufficient to produce hydrolysis of said protein by said at least one enzyme, so as to produce a product containing solubilized hydrolyzed protein and insoluble chromium, wherein said at least one enzyme is active against said protein at said conditions sufficient to produce hydrolysis of said protein by said at least one enzyme.

3. The method of either claim 1 or 2 wherein said hydrolysis takes place at a pH of from about 8 to about 11.

4. The method of claim 3 wherein said hydrolysis takes place at a pH of from about 8.3 to about 9.3.

5. The method of either claim 1 or 2 wherein said hydrolysis is carried out for a period of time of from about 1 minute to about 4 hours.

6. The method of claim 5 wherein said hydrolysis is carried out for a period of time from about 2 hours to about 3 hours.

7. The method of either claim 1 or 2 wherein said hydrolysis is carried out at a temperature of from about 50° C. to about 75° C.

8. The method of claim 7 wherein said hydrolysis is carried out at a temperature of from about 63° C. to about 65° C.

9. The method of either claim 1 or 2 wherein said step of holding is carried out for a said period of time from about 1 hour to about 2 hours.

10. The method of either claim 1 or 2 wherein said material contains insoluble chromium.

11. The method of claim 10 wherein said material contains a chromium containing composition selected from the group consisting of blue stock, chrome shavings, chrome buffing dust, chrome cakes and chrome sludges.

12. The method of either claim 1 or 2 wherein said step of combining is carried out with sufficient water to produce a mixture containing from about 77 weight % water to about 91 weight % water.

13. The method of either claim 1 or 2 further including the step of separating insoluble chromium from said product.

14. The method of claim 13 wherein said step of separating is selected from the group consisting of, gravitational settling, filtration or centrifugation, of said product.

15. The method of claim 13 further including the steps of: solubilizing the separated insoluble chromium in an acid, and utilizing the solubilized chromium in acid to pickle a hide.

16. The method of claim 13 further including the steps of: solubilizing the separated insoluble chromium in an acid, precipitating the chromium from said acid, and utilizing the precipitated chromium to tan a hide.

17. The method of either claim 1 or 2 wherein said material to be treated contains solubilized chromium.

18. The method of claim 2 wherein said additive consists essentially of one or more of magnesium oxide or magnesium hydroxide, and wherein said step of combining includes combining said material with an amount of said additive sufficient to bring the pH of said mixture into the range of from about 8.9 to about 9.1.

19. The method of claim 2 wherein said additive includes one or more of magnesium oxide or magnesium hydroxide and one or more of calcium oxide or calcium hydroxide, and wherein said step of combining includes combining said material with an amount of said additive sufficient to bring the pH of said mixture into the range of from about 9.2 to about 10.4.

20. The method of claim 2 wherein said additive includes magnesium oxide and sodium hydroxide.

21. The method of claim 2 wherein said additive includes magnesium oxide and sodium carbonate, and wherein said step of combining includes combining said material with an amount of said additive sufficient to bring the pH of said mixture into the range of from about 9 to about 10.

* * * * *